(12) United States Patent
Evans et al.

(10) Patent No.: US 7,204,993 B2
(45) Date of Patent: Apr. 17, 2007

(54) STREPTOCOCCUS AGALACTIAE VACCINE

(75) Inventors: Joyce J. Evans, Chestertown, MD (US); Phillip H. Klesius, Auburn, AL (US); Craig A. Shoemaker, Notasulga, AL (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 188 days.

(21) Appl. No.: 10/807,575

(22) Filed: Mar. 18, 2004

(65) Prior Publication Data

US 2005/0208077 A1      Sep. 22, 2005

(51) Int. Cl.
 *A61K 38/00*  (2006.01)
 *A61K 39/09*  (2006.01)
 *A61K 39/085* (2006.01)
 *A61K 39/02*  (2006.01)
 *A61K 39/00*  (2006.01)
 *A01N 63/00*  (2006.01)
 *A01N 37/18*  (2006.01)

(52) U.S. Cl. .............. 424/244.1; 424/184.1; 424/234.1; 424/236.1; 424/237.1; 424/93.1; 424/93.4; 424/93.44; 514/2

(58) Field of Classification Search ........... 424/184.1, 424/234.1, 236.1, 237.1, 244.1, 93.4, 93.1, 424/93.44; 514/2
See application file for complete search history.

(56) References Cited

U.S. PATENT DOCUMENTS 4,425,330 A * 1/1984 Norcross et al. ......... 424/203.1
6,379,677 B1    4/2002 Klesius et al.

FOREIGN PATENT DOCUMENTS

WO    WO 2005/089447 A2 *  9/2005

OTHER PUBLICATIONS

Evans et al, Vaccine, 2004, 22:3769-3773.*
Dal et al, FEMS Microbiology Letters, 1983, 16:89-94.*
Chun-Yao, Dai-B, Jun. 2003, 63/12:5709 dissertation abstract only.*
de la Rosa et al, J. Clinical Microbiology, 1992, 30/4:1019-1021.*
Neely et al, Infection and Immunity, 2002, 70/7:3904-3914.*
Kawamura et al, Int. J. Sys. Evol. Microbiol., 2005, 55:961-965.*
Hagaki et al, Int. J. Tissue React., 2003, XXV/2:47-50.*
Miller et al, Acta Tropica, 2004, 91:53-68.*
Berridge et al, Vet. Microbiol., 2001, 78:165-173.*
Zlotkin et al, Applied and Environ. Microbiology, 1998, 64/10:4065-4067.*
Ezaki et al, Int. J. Sys. Bacteriol., 1986, 36/2:345-347.*
Berridge, Dai-B, Feb. 1999, 59/08:3789 dissertation abstract only.*
Nakanishi et al, Vaccine, 2002, 20:3764-3769.*
Pasnik et al, J. Fish Diseases, Apr. 2005, 28/4:205 abstract only.*
Evans et al, Aquaculture, 2004, 233(1-4):15-21 abstract only.*
Evans et al, Aquaculture, 2004, 233:15-21.*
Kawamura et al, International J. Systematic & Evolutionary Microbiology, 2005, 55:961-965.*
Pasnik et al, J. Fish Diseases, 2005, 28:205-212.*
Pasnik et al, Fish & Shellfish Immunology, 2006, pp. 1-7 (Article In Press).*
Pasnik et al, Diseases of Aquatic Organisms, 2005, 66:129-134.*
Abid et al, Lymphokine and Cytokine Research, 1991, 10/1:43-50.*
Teska et al, Biomedical Letters, 1994, 50:195-201.*
Berrodge et al, Vet. Microbiology, 2001, 78:165-173.*
Kawamura et al, Antimicrobial Agents and Chemotherapy, Nov. 2003, 47/11:3605-3609.*
Passnik et al, Fish & Shellfish Immunology, 2006, 21:365-371.*
Hughes et al, FEMS Microbiology Letters, 2003, 222:263-271.*
Evans et al, J. Fish Diseases, 2002, 25:505-513.*
Tikkanen et al, J. Immunological Methods, 1995, 187:233-244.*
Spellerberg, Microbes and Infection, 2000, 2:1733-1742.*
Jarva et al, Molecular Immunology, 2003, 40:95-107.*
Pasnik et al, J. Fish Disease, Apr. 2005, 28/4:205/212 (Abstract Only).*
Avi Eldar et al., "Experimental Streptococcal Meningo-Encephalitis in Cultured Fish," *Veterinary Microbiology 43* (1995) pp. 33-40.
P.H. Klesius et al., "Vaccination Stress in Nile Tilapia, *Oreochromis niloticus,*" Presented at the European Associated Fish Patrol in Sep. 22-23, 2003.
A. Eldar et al., "Development and Efficacy of a Vaccine Against *Streptococcus iniae* Infection in Farmed Rainbow Trout," *Veterinary Immunology and Immunopathology 56* (1997) pp. 175-183.

(Continued)

*Primary Examiner*—Nito Minnifield
(74) *Attorney, Agent, or Firm*—John Fado; Randall E. Deck; Lesley Shaw (57) ABSTRACT

A composition prepared from intact killed cells of isolated β-hemolytic *Streptococcus agalactiae* and a concentrated extract of a culture of β-hemolytic *Streptococcus agalactiae*, is effective for the protection of fish against infection by the same and other virulent strains *Streptococcus agalactiae*.

18 Claims, 4 Drawing Sheets

OTHER PUBLICATIONS

J.J. Evans et al., "Characterization of β-haemolytic Group B *Streptococcus agalactiae* in cultured seabream, *Sparus auratus* L., and Wild Mullet, *Liza klunzingeri* (Day), in Kuwait," *Journal of Fish Diseases 2002*, 25, 505-513.

P. Vandamme et al., "*Streptococcus difficile* is a Nonhemolytic Group B, Type lb *Streptococcus,*" *International Journal of Systematic Bacteriology*, Jan. 1997, pp. 81-85, vol. 47, No. 1.

Avi Eldar et al., "Vaccination with Whole-Cell Vaccine and Bacterial Protein Extract Protects Tilapia against *Streptococcus difficile* meningoencephalitis," *Vaccine* vol. 13, No. 9, pp. 867-870, 1995.

M. Akhlaghi et al., "Comparison of Passive and Active Immunization of Fish against Streptococcosis (Enterococcosis)," *Journal of Fish diseases 1996*, 19, pp. 154-258.

Donald F. Amend, "Potency Testing of Fish Vaccines," International Symposium in Fish Biologics: Serodiagnostics and Vaccines, Leetown, W. VA, 1981, *Develop. Biol. Standard*, 49, pp. 447-454 (S. Karger, Basel 1981).

A.M. Baya et al., "Association of *Streptococcus* sp. with Fish Mortalities in the Chesapeake Bay and its Tributaries," *Journal of Fish Diseases 1990*, 13, pp. 251-253.

H. Bercovier et al., "Immunization with Bacterial Antigens: Infections with Streptococci and Related Organisms," Gudding R. Lillehaug A. Midtlyng PJ, Brown F (eds): Fish Vaccinology.. *Dev Biol Stand. Basel, Karger*, 1997, vol. 90, pp. 153-160.

David W. Cook et al., "Pathogenicity Studies with a *Streptococcus* sp. Isolated from Fishes in an Alabama-Florida Fish Kill," *Trans. Amer. Fish. Soc.*, 1975, No. 2 pp. 286-288.

John A. Elliott et al., "Whole-Cell Protein Patterns of Nonhemolytic Group B, Type lb, Streptococci Isolated from Humans, Mice, Cattle, Frogs, and Fish," *Journal of Clinical Microbiology*, Mar. 1990. pp. 628-630

Patricia M. Glibert et al., "A Fish Kill of Massive Proportion in Kuwait Bay, Arabian Gulf, 2001: the Roles of Bacterial Disease, Harmful Algae, and Eutrophiction," *Harmful Algae 1* (2002) 215-231.

Phillip H. Klesius et al., "Efficacy of Single and Combined *Streptococcus iniae* Isolate Vaccine Administered by Intraperitoneal and Intramuscular Routes in Tilapia (*Oreochromis niloticus*)," *Aquaculture 188* (2000) 237-246.

Phillip H. Klesius et al., "Efficacy of a Killed *Streptococcus iniae* Vaccine in Talapia (*Oreochromis niloticus*)," *Bull. Eur. Ass. Fish Pathol.*, 19(1),39,1999.

Riichi Kusuda et al., "A Comparative Study of Fish Pathogenic *Streptococcus* Isolated from Saltwater and freshwater Fishes," *Bulletin of the Japanese Society of Scientific Fisheries 44*(10) 1073-1078 (1978).

Teruyuki Nakanishi et al., "Development of a New Vaccine Delivery Method for Fish: Percutaneous Administration by Immersion with Application of a Multiple Puncture Instrument," *Vaccine 20* (2002) 3764-3769.

J.A. Plumb et al., "*Streptococcus* sp. from Marine Fishes Along the Alabama and Northwest Florida Coast of the Gulf of Mexico," *Transactions of American Fisheries Society 2*, 358-361.

Victoria Rasheed et al., "histopathology of Bullminnows, *Fundulus grandis* Baird & Girard, Infected with a Non-haemolytic Group B *Streptococcus* sp.," *Journal of Fish Diseases 1985*, 8, 65-74.

Victoria Rasheed et al., "Pathogenicity of a Non-haemolytic Group B *Streptococcus* sp. in Gulf Killifish (*Fundulus grandis* Baird and Girard)," *Aquaculture*, 37 (1984) 97-105.

Jordan A. Robinson et al., "Streptococcal Fish Pathogen," *Journal of Bacteriology*, Aug. 1966 vo. 92, No. 2 p. 512.

Romalde, J.L. et al., "Prevention of Streptococcosis in Turbot by Intraperitoneal Vaccination: a review," *J. Appl. Ichthyol. 15*, 153-158.

Jesus L. Romalde et al., "Long-Lasting Protection Against Turbot Streptococcosis Obtained with a Toxoid-Enriched Bacterin," *Bull Eur. Ass. Fish pathol.*, 16(5), 169, 1996.

A.E. Toranzo et al., "Efficacy of Intraperitoneal and Immersion Vaccination against *Enterococcus* sp. Infection in Turbot," *Aquaculture 134*:17-27.

P. Vandamme et al., "*Streptococcus difficile* is a Nonhemolytic Group B, Type lb *Streptococcus,*" *International Journal of Systematic Bacteriology Jan. 1997* pp. 81-85 vol. 47 No. 1.

Hazel W. Wilkinson et al., "Nonhemolytic Group B Streptococci of Human, Bovine, and Ichthyic Origin," *Infection and Immunity Mar. 1973* vol. 7, 496-498.

\* cited by examiner

STREPTOCOCCUS AGALACTIAE VACCINE

BACKGROUND OF THE INVENTION

1. Field of the Invention

The invention relates to novel vaccines for protecting fish against infection with *Streptococcus agalactiae*, and a novel process for making the same.

*Streptococcus agalactiae* is a Group B streptococcal bacterium that causes severe economic losses in a number of species of cultured and wild fish. This infectious bacterium is common in aquaculture facilities where fish are intensively cultured in fresh, brackish, or marine waters. The high densities of fish and the aqueous environment favor the rapid transmission of streptococcal disease. Moreover, infected cultured fish may transmit the disease to wild fish populations, or infected wild fish may transmit the disease to cultured fish.

2. Description of the Prior Art

Vaccines have previously been developed against various *Streptococcus* and *Enterococcus* species utilizing strategies based on either intraperitoneal or intramuscular injection. Several injectable vaccines have been developed for the prevention of streptococcosis, although many of these vaccines differ in their formulation. Protection of rainbow trout after intraperitoneal (IP) vaccination with a formalin killed *Streptococcus iniae* vaccine was reported by Eldar et al. (Development and efficacy of a vaccine against *Streptococcus iniae* infection in farmed rainbow trout, Vet Immunol Immunopathol 1997; 56: 175–183). Klesius et al. [Efficacy of a killed *Streptococcus iniae* vaccine in tilapia (*Oreochromis niloticus*), Bull Eur Ass Fish Pathol 1999; 19(1): 38–41; and Efficacy of a single and combined *Streptococcus iniae* isolate vaccine administered by intraperitoneal and intramuscular routes in tilapia (*Oreochromis niloticus*), Aquaculture 2000; 188(3–4): 237–246] have developed a modified killed *S. iniae* vaccine composed of whole cells and concentrated, extracellular products. Immunized 25 g tilapia (*Oreochromis niloticus*) had a relative percent survival (RPS) of 95.3 and 100 g tilapia had RPS values ranging from 84.2 to 94. Turbot (*Scophthalmus maximus*) were protected against *Enterococcus* sp. after vaccination with a toxoid-enriched bacterin [Romalde et al., Prevention of streptococcosis in turbot by intraperitoneal vaccination: A review, J Appl Ichthyol 1999; 15: 153–158; Long-lasting protection against turbot streptococcosis obtained with a toxoid-enriched bacterin, Bull Eur Ass Fish Pathol, 1996; 16(5): 169–171; and Toranzo et al., Efficacy of intraperitoneal and immersion vaccination against *Enterococcus* sp. infection in turbot, Aquaculture 1995; 134: 17–27]. The toxoid-enriched bacterin vaccine was a combination of two formalin-killed *Enterococcus* sp. isolates and their culture fluids. Rainbow trout (*Oncorhynchus mykiss*) immunized with formalin-killed *Streptococcus* sp. in Freund's incomplete adjuvant were protected against *Streptococcus* sp., whereas trout immunized by bath immersion were not protected [Akhlaghi et al., Comparison of passive and active immunization of fish against streptococcosis (enterococcosis), J Fish Dis 1996; 19: 251–258]. Recently, Nakanishi et al. (Development of a new vaccine delivery method for fish: Percutaneous administration by immersion with application of a multiple puncture instrument, Vaccine 2002; 20: 3764–3769) demonstrated the protection of skin punctured juvenile rainbow trout immersed in a formalin killed *S. iniae* vaccine suspension rivaled that obtained by IP injection.

Eldar et al. disclosed the preparation of an injectable vaccine prepared from formalin-killed *Streptococcus difficile*. This vaccine was reported to protect tilapia (*Oreochromis* sp.) against challenge with *S. difficile* [Eldar et al., Vaccination with whole-cell vaccine and bacterial protein extracts protects tilapia against *Streptococcus difficile* meningoencephalitis, Vaccine 1995; 13(9): 867–870; and Bercovier et al., Immunization with Bacterial Antigens: Infections with Streptococci and Related Organisms; Fish Vaccinology, Dev. Biol. Stand., Vol. 90 (Liiehaug, G., Midlyng, P J & Brown, F. eds.) Karger, Basel, Switzerland, pp. 153–160, 1997].

In a subsequent report however, Vandamme et al. (*Streptococcus difficile* is a nonhemolytic group B, type Ib *Streptococcus*, Int J Syst Bacteriol, 1997; 47(1): 81–85), proposed that the *S. difficile* reported by Eldar et al. was actually a non-hemolytic, group B *Streptococcus, S. agalactiae*. Indeed, many of the reported streptococcal fish isolates originally unspeciated or misidentified have been more recently characterized as non-hemolytic, group B *Streptococcus, S. agalactiae*.

SUMMARY OF THE INVENTION

We have now discovered novel vaccines that are safe and effective for the control of *Streptococcus agalactiae* in fish, particularly tilapia (*Oreochromis niloticus*) and other species of fish susceptible to *S. agalactiae* infection. The vaccines comprise intact (whole) killed cells of one or more β-hemolytic isolates of *Streptococcus agalactiae*, and the concentrated extract from a culture of a β-hemolytic *Streptococcus agalactiae*. The vaccine composition is effective for the protection of fish against infection by the same or other virulent strains *Streptococcus agalactiae* (i.e., different from the isolate(s) of *S. agalactiae* used to prepare the vaccine).

In accordance with this discovery, it is an object of the invention to provide a novel, highly protective, vaccine against *S. agalactiae* for fish.

Another object of this invention is to provide a vaccine which is effective in preventing epizootics in fish populations caused by *S. agalactiae*.

Yet another object of this invention is to provide an effective vaccine against *S. agalactiae* which may be administered by injection or bath immersion.

Yet another object of this invention is to provide both monovalent and polyvalent vaccines against *S. agalactiae* isolates having increased efficacy.

An additional object of this invention is to provide novel isolates of β-hemolytic *S. agalactiae* from fish which may be used for the preparation of vaccines against *S. agalactiae* infection in fish.

A still further object of this invention is to improve the viability and productivity of tilapia, striped bass and other fish species, and to reduce economic losses thereto caused by *S. agalactiae*.

Other objects and advantages of the invention will become readily apparent from the ensuing description.

DEPOSIT OF BIOLOGICAL MATERIAL

Beta hemolytic, encapsulated *S. agalactiae* brain isolates (ARS-KU-3 B and ARS-KU-11 B) were deposited on Jul. 17, 2002, under the provisions of the Budapest Treaty in the Agricultural Research Service Culture Collection located at 1815 North University Street, Peoria, Ill. 61604, and have been assigned Deposit Accession No.'s NRRL B-30608 and NRRL B-30607, respectively.

As used herein, *Streptococcus agalactiae* refers to the recognized species, the characteristics of which are described by Evans et al. (Characterization of β-haemolytic Group B *Streptococcus agalactiae* in cultured seabream, *Sparus auratus* L., and wild mullet, *Liza klunzingeri* (Day), in Kuwait, Journal of Fish Diseases 2002; 25:505–513, the contents of which are incorporated by reference herein), and other reference strains of which have been deposited at the American Type Culture Collection, Manassas, Va., USA.

DETAILED DESCRIPTION OF THE INVENTION

As used herein, "vaccine" is defined in its broad sense to refer to any type of biological agent in an administratable form capable of stimulating a protective immune response in an animal inoculated with the vaccine.

The present invention provides novel vaccines comprising one or more killed, β-hemolytic isolates of *S. agalactiae* in the form of intact (whole) cells, in combination with a concentrated extract from a culture of the same or different isolate of β-hemolytic *S. agalactiae*. The vaccines are effective for controlling infection of fish by any strain of *S. agalactiae*, including strains which are different from those used in the preparation of the vaccine. Moreover, the vaccines are effective for controlling infections by β-hemolytic and non-hemolytic strains, as well as encapsulated or non-encapsulated strains. However, the vaccine is particularly effective for eliciting a protective response in fish against infection by β-hemolytic strains of *S. agalactiae*.

The vaccines of this invention are effective in controlling infection by *S. agalactiae* in a variety of fish when administered thereto. Vaccination also significantly reduces abnormal behavior and morphology in the treated fish. Without being limited thereto, the vaccine is especially beneficial for the treatment of domestic or exotic fish, including golden shiners, bullminnows, bluefish, gulf menhaden, sea catfish, mullet, pinfish, Atlantic croaker, spot, weakfish, channel catfish, rainbow trout, eels, striped bass and their hybrids, sea bass, sea bream, turbot, and tilapia.

The particular strain of β-hemolytic *S. agalactiae* used for preparation of the vaccines is not critical, and any beta-hemolytic, encapsulated or non-encapsulated, isolate of *Streptococcus agalactiae* is suitable for use herein. Suitable *S. agalactiae* may be isolated from environmental or natural sources such as infected fish using conventional and enrichment techniques similar to those described by Evans et al. (Characterization of β-haemolytic Group B *Streptococcus agalactiae* in cultured seabream, *Sparus auratus* L., and wild mullet, *Liza klunzingeri* (Day), in Kuwait, Journal of Fish Diseases 2002; 25:505–513, the contents of which are incorporated by reference herein), or from previously isolated substantially pure strains. Preferred strains include those which are encapsulated, particularly the above-mentioned strains NRRL B-30608 and NRRL B-30607. While efficacy has been shown with both monovalent and polyvalent vaccines, polyvalent systems prepared using more than one strain of β-hemolytic *S. agalactiae* are preferred due to the indicated antigenic heterogeneity that may exist in the species.

The inventive vaccine is a killed cell preparation or bacterin, which also includes a concentrated fraction of the extracellular filtrate (cell-free culture fluid) of a culture of *S. agalactiae*. As such, the concentrated fraction is substantially free of cells, cell wall fragments, and intracellular components of *S. agalactiae*. Although the cells are removed from the concentrated fraction, the skilled practitioner will recognize that a relatively small amount of intracellular products and cell wall fragments may be present as the result of normal cell lysis occurring during the course of culture. In a particularly preferred embodiment, low molecular weight extracellular components (as well as any low molecular weight intracellular components) are removed from the concentrated fraction, preferably those having a molecular weight less than about 1 kDa, more preferably those having a molecular weight less than about 2 kDa, and most preferably those having a molecular weight less than about 3 kDa. Without wishing to be bound to theory, it is believed that various low molecular weight components of the extracellular products of killed *S. agalactiae* have an inhibitory effect upon the antigenicity of the bacterin suspensions. Concentration and filtration of the extracellular retentate substantially removes these inhibitory components and thus increases efficacy of the vaccine. In addition, the extracellular products are believed to include antigens from the capsule or secreted/excreted antigens and other beneficial molecules providing a superior immunization response.

Propagation of the bacterium for preparation of the vaccine may be effected by culture under any conventional conditions and on media which promote its growth. Although a variety of conventional solid and liquid media may be suitable for use herein, growth in liquid culture is particularly preferred for large scale production. Without being limited thereto, conventional tryptic soy broth is preferred, although additional nutrients may be added to enhance capsule (polysaccharide) production. For example, the addition of sugar such as glucose may enhance polysaccharide production. The production of the vaccine may be conducted by stationary culture of the selected isolate without adjusting the culture pH during the fermentation at 25° C. for 5 to 7 days. Starving *S. agalactiae* cells, by a prolonged fermentation time of 5 to 7 days, is also believed to enhance the efficacy of the resultant vaccine, and thus is preferred. The final pH value of the vaccine prepared in this medium may range from pH 6.5 to 7.4. The salinity of the vaccine preparation is preferably in the range of 3.6–4.0 parts per thousand (ppt) salt (YSI Incorporated, Yellow Springs, Ohio) and it is believed that this property may also enhance the effectiveness of the vaccine, especially when administered by the bath immunization method. Without being limited thereto, the vaccine (produced as described in Example 2) measured by a clinical refractometer (Atago A300CL, Vee Gee Scientific, Inc., Kirkland, Wash.) is 1.3384 to 1.3387 on the serum protein (g/100 ml) scale; is 1.015 to 1.016 on the urine specific gravity (UG) scale and refractive index (nD) at 589 nanometers (nm) is 1.0 to 1.2. The optical density (OD) of the vaccine at 540 nm (UV-Visible Spectrophotometers, Spectronic Unicam, Cambridge, UK) is in the range of 0.887 to 0.939. Aeration is generally not preferred. All vegetable based fermentation media are also preferred for use herein, as the use thereof eliminates the risks of the presence of animal products and infectious agents in the final vaccine product.

Following their propagation and recovery, cells of *S. agalactiae* are subjected to chemical and/or physical treatment effective to kill (i.e., inactivate) the cells. An effective treatment for killing the cells is defined herein as that which kills 99.9% or more of the viable cells, without lysing the cells and while retaining the ability of the cells to elicit an antibody response in the animal. Thus, the treatment should not substantially alter the specificity of the cell surface antigens on the killed cells relative to the untreated cells. While treatments killing 100% of all viable cells would typically be preferred, the skilled practitioner will recognize 100% cell death may not always be readily obtainable. In the preferred embodiment, killed, intact *S. agalactiae* are prepared by treatment of the viable cells with formalin. Alternatively, the cells may be killed by UV irradiation such as described by Purdy et al. (U.S. Pat. No. 6,303,130) for the preparation of *Pasteurella haemolytica* bacterins. It is also envisioned that a variety of other techniques have been described for the preparation of killed cell vaccines (i.e., bacterins) are also suitable for use herein, and include but are not limited to treatment with alcohols, particularly an aliphatic alcohol such as ethanol or isopropyl alcohol, phenol, tricresol, formalin, formaldehyde, acetone, merthiolate, β-lactones, and moderate heat at temperatures which would not induce protein denaturation (e.g., 56° C. for 1 hour). Treatment times and conditions will of course vary with the particular method selected and may be readily determined by routine testing.

In the preferred embodiment, the *S. agalactiae* cells in their fermentation container are exposed to formalin for a sufficient period of time to kill 100% of the cells. Typically, formalin concentration would range from about 1% to about 5% (v/v), preferably from about 1% to about 3% (v/v). Suitable exposure times for a particular formalin concentration to achieve 100% killing may be readily determined from lethal killing curves of % killed vs. time of treatment.

Following fermentation, the cells are concentrated, for example, by filtration or centrifugation to obtain a high density suspension of cells, and the cell pellet and fermentation culture fluid are separated. The separated cells may be retained for use as the first component of the vaccine. The filtrate, in the form of the cell-free culture fluid, is then itself subjected to another concentration step to produce the concentrated extract, and preferably to remove the above-mentioned low-molecular weight extracellular components. A variety of filtration systems, with different molecular weight cut-offs, are suitable for use in this preferred embodiment. Preferred filters include those having a molecular weight cut-off of approximately 1 kDa, producing a concentrated extract comprising extracellular products from the culture having a molecular weight greater than about 1 kDa. Use of filters having molecular weight cut-offs of approximately 2 kDa are more preferred, with those having a cut-off of approximately 3 kDa being particularly preferred, producing concentrated extracts comprising extracellular products from the culture with molecular weights greater than about 2 and 3 kDa, respectively. In one preferred embodiment, the cell-free culture fluid is concentrated by use of a 3 kDa Amicon column (S3Y3) using a Millipore Proflux M12 (Billerica, Mass.). In any filtration system, separation may be carried out to completion, with water added to re-suspend the retentate. In a particularly preferred embodiment, separation may be carried out until there has been a five-fold reduction in retentate volume. This leaves adequate water in the retentate so that suspension of the previously retained cell pellet readily occurs upon recombination with the retentate (i.e., the concentrated extract). For convenience, it is envisioned that the killed cells and concentrated extract will typically be prepared from the same culture. However, it is recognized that they may be prepared from different cultures of the same or different strains of *S. agalactiae*.

Appropriate ratios may be determined by those skilled in the art, but are seen to typically range from about 5:1 (vol/vol) to about 20:1 (vol/vol), preferably about 10:1 (vol/vol) of the original fermentation cell-free culture fluid [i.e., the ratio of the original volume of the cell-free culture fluid to the concentrated culture fluid (retentate) volume]. The concentrated cell-free culture fluid is sterilized using a 0.22 Fm 1 l microbiological filter (Corning, Corning, N.Y.). Sixteen ml of the formalin-killed cells are added to 1000 ml of the sterilized concentrated cell-free fermentation fluid.

Following re-suspension of the cell pellet in the retentate, the killed *S. agalactiae* cells are prepared for administration by formulation in an immunologically effective amount or dosage to the fish. The dose may either be given as simply the retentate containing the re-suspended killed cells, or may further include pharmaceutically acceptable carriers and adjuvants known in the art. An immunologically effective amount or dosage is defined herein as being that amount which will induce complete or partial immunity (elicit a protective immune response) in a treated fish against subsequent challenge with virulent strain of *S. agalactiae*. Immunity is considered as having been induced in a population of treated animals when the level of protection for the population (evidenced by a decrease in the number of infected fish or a decrease in the severity of infection) is significantly higher than that of an unvaccinated control group (measured at a confidence level of at least 80%, preferably measured at a confidence level of 95%). The appropriate effective dosage can be readily determined by the practitioner skilled in the art by routine experimentation. Typically, the vaccine will contain at least $1 \times 10^8$ cells of *S. agalactiae*/ml of bath medium, preferably about $4 \times 10^9$ cells of *S. agalactiae*/ml of bath medium. Depending on fish size, for an IP injection routine, a preferred dose in a fish would be about 0.1–0.2 ml of the amount above. Although greater amounts of cells may be administered, use of such higher levels is generally considered impractical.

The killed cells are prepared for administration by formulation in a pharmaceutically acceptable carrier such as water, physiological saline, mineral oil, vegetable oils, aqueous sodium carboxymethyl cellulose, or aqueous polyvinylpyrrolidone. The vaccine formulations may also contain optional adjuvants, antibacterial agents or other pharmaceutically active agents as are conventional in the art. Without being limited thereto, suitable adjuvants include but are not limited to mineral oil, vegetable oils, alum, and Freund's incomplete adjuvant. Still other preferred adjuvants include microparticles or beads of biocompatible matrix materials. The microparticles may be composed of any biocompatible matrix materials as are conventional in the art, including but not limited to, agar and polyacrylate. The practitioner skilled in the art will recognize that other carriers or adjuvants may be used as well. For example, other adjuvants which may be used are described by Webb and Winkelstein [in *Basic & Clinical Immunology*, Stites et al. (ed.), fifth edition, Lange Medical Publications, Los Altos, Calif., 1984, pages 282–285], the contents of which are incorporated by reference herein.

In accordance with a preferred embodiment, the killed cells may be incorporated into microparticles or microcapsules to prolong the exposure of the antigenic material to the subject animal and hence increase the duration of protective immunity. The microparticles and capsules may be formed from a variety of well-known inert, biocompatible matrix materials using techniques conventional in the art. Without being limited thereto, suitable matrix materials include natural or synthetic polymers such as alginates, poly(lactic acid), poly(lactic/glycolic acid), poly(caprolactone), polycarbonates, polyamides, polyanhydrides, polyortho esters, polyacetals, polycyanoacrylates, polyurethanes, ethylene-vinyl acetate copolymers, polystyrenes, polyvinyl chloride, polyvinyl fluoride, poly(vinyl imidazole), chlorosulphonated polyolefins, polyethylene oxide, and particularly agar and polyacrylates. Examples of techniques for incorporation of material into microparticles or encapsulation which may be used herein are described by Sparks [Microencapsulation, In: Kirk-Othmer Encyclopedia of Chemical Technology, third edition, John Wiley & Sons, New York, (1981), volume 15, pages 470–493], Kydonius [controlled Release Technologies: Methods, Theories, and Applications, CRC Press, Cleveland, Ohio, 1980], Gombotz et al. [U.S. Pat. No. 5,019,400], or Beck [U.S. Pat. No. 4,919,929], the contents of each of which are incorporated by reference herein.

The vaccines of the invention may be administered to the subject animal by any convenient route which enables the cells to elicit an immune response, such as by intraperitoneal or intramuscular injection, bath immersion, oral administration, or nasal administration. However, intraperitoneal injection or bath immersion is preferred for primary immunization, while oral immunization is preferred for secondary or booster immunization, when necessary. It is also envisioned that the surface of the fish may be punctured such as described by Nakanishi et al. (2002, ibid) or otherwise abraded or slightly descaled, prior to or during bath immersion, to facilitate exposure of the vaccine to the animal's immune system. The vaccine may be administered in a single dose or in a plurality of doses. Dependent upon rearing conditions, the vaccine may be administered in multiple doses, the timing of which may be readily determined by the skilled artisan.

Vaccination against infection by *S. agalactiae* by bath immersion immunization offers several advantages over other routes of immunization. Among these advantages are lower cost per fish immunized, mass immunization of large numbers of fish, reduced stress, significantly higher rates of fish survival and the absence of adverse reactions to vaccination. Furthermore, bath immersion vaccination is an effective method for mass vaccination of smaller fish that can not be injected or subjected to skin punctures. Alternatively, intraperitoneal injection of commercially available fish vaccines is commonly employed on fresh or marine aquaculture farms due to their reliability and high efficacy despite high cost per fish immunized and stress to the fish.

The following examples are intended only to further illustrate the invention and are not intended to limit the scope of the invention which is defined by the claims.

EXAMPLE 1

The *S. iniae* vaccine developed previously by Klesius et al. was evaluated for efficacy against *S. agalactiae*. The vaccine was not protective.

Materials and Methods

The tilapia were from stocks maintained at the ARS, USDA, Aquatic Animal Health Research Laboratory (Auburn, Ala.). Tilapia with mean weights of five and 30 g were acclimated in flow-through 57 l glass aquaria supplied with 0.5 l/h de-chlorinated water for 10 days prior to experiments. A light and dark period of 12 h: 12 h was maintained and aeration was supplied by an air stone. The fish were fed daily to satiation with AQUAMAX GROWER 400 (Brentwood, Mo.). Water quality was monitored, with dissolved oxygen, temperature and salinity measured daily using a YSI 85 oxygen conductivity, salinity, and temperature meter (Yellow Spring Instrument Co., Yellow Springs, Ohio). Daily water temperature averaged 26.3±0.03° C. and mean daily dissolved oxygen was 5.95±0.06 mg/l. To verify the *S. agalactiae*-free status of the fish, samples were obtained for bacterial culture by passing an inoculation loop into brain and kidney. Samples were streaked directly on sheep blood agar that were incubated at 27° C. for 24 to 48 h. *S. agalactiae* was not isolated from five randomly selected fish.

Vaccine Preparation

The preparation of the *S. iniae* vaccine was previously described (Klesius et al., Efficacy of a killed *Streptococcus iniae* vaccine in tilapia (*Oreochromis niloticus*), Bull Eur Ass Fish Pathol, 1999; 19(1): 38–41.1999). Briefly, vaccines were prepared by separate culture of *Streptococcus iniae* isolates (NRRL B-30264 and NRRL B-30238) in tryptic soy broth (TSB) and incubated in a shaker (70 RPM) water bath at 27° C. for 72 hours. Cultures were treated with 10% neutral buffered formalin to give a final concentration of 3% at 27° C. for 24 hours. The formalin treated cultures were centrifuged at 7000×g for 30 minutes and cell pellet and culture fluid separated. The cell free culture fluid was concentrated 20 fold using a 2 kDa hollow fiber concentrator to remove all components of lower molecular weight. This 2 kDa culture fluid concentrate was then used to re-suspend the cell pellet at V/V of 10:1. The final concentration of the vaccine was $4 \times 10^9$ CFU/ml. The bacterial concentration was estimated by taking the optical density of the vaccine prior to killing by formalin. The actual number of CFU/ml was determined using a spiral autoplater and Qcount (Spiral Biotech, Norwood, Mass.). Non-vaccinates received concentrated tryptic soy broth (TSB) only. The vaccine cells were determined to be killed by lack of growth on sheep blood agar at 72 hours.

Vaccination Protocol

To determine whether the *S. iniae* vaccine was protective against *S. agalactiae*(trial 1), two hundred tilapia with mean weight of 30 g were divided into 10 tanks of 20 fish each, including non-immunized controls (Table 1). Five replicate tanks of tilapia served as controls. The *S. iniae* NRRL B-30264 or the combined NRRL B-30264/NRRL B-30238 vaccines were intraperitoneally injected in a volume of 0.1 ml into tilapia. Control tilapia received 0.1 ml of TSB. Immunized and control tilapia were held for 30 days before challenge. The tilapia were monitored for mortality for 14 days post-challenge.

Experimental *S. agalactiae* Challenge and Bacteriologic Sample Collection and Evaluation

*Streptococcus agalactiae* isolate NRRL B-30607 originally isolated from wild Klunzingeri mullet, *Liza Klunzingeri* (Day), with natural streptococcal disease was used to infect fish. The isolate was identified as *S. agalactiae* by standard methods. The *S. agalactiae* isolated from mullet (*Liza klunzingeri*), designated ARS-KU-11B (National Agricultural Research Collection NRRL B-30607), was grown in tryptic soy broth (TSB, Difco Laboratories, Sparks, Md.) for 24 h at 27° C. and then frozen in 0.2 ml aliquots at −70° C. The infectious isolate used in this study was prepared by inoculating TSB with a thawed aliquot of the frozen isolate.

Fish were then challenged with $2.6 \times 10^5$ CFU/ml by IP injection with 100 µl *S. agalactiae*. Dead fish were removed twice a day and at postmortem examination, specimens were obtained aseptically from brain, anterior kidney and intestines. Specimens were cultured directly onto sheep blood agar at 27® C. for 24 to 48 h. Beta-hemolytic, catalase-negative and Gram-stained positive coccus colonies were sub-cultured onto sheep blood agar and then bacteriologically and biochemically identified as *S. agalactiae* according to tests described by Evans et al., (Characterization of beta-haemolytic Group B *Streptococcus agalactiae* in cultured seabream, *Sparus auratus* (L.) and wild mullet, *Liza klunzingeri* (Day), in Kuwait, J Fish Dis, 2002; 25: 505–513) herein incorporated by reference. All tests were conducted at 27° C. using media purchased from Remel (Lenexa, Kans.).

The mean percent mortality and mean percent cumulative mortality of vaccinated and non-vaccinated tilapia for each trial was determined over a 14 d period. The efficacy of the vaccine was calculated as the relative percent survival (RPS) according to Amend (1981).

Statistical Analysis

Randomization of treatment tanks was performed using a block design described by Gomez and Gomez. All data were examined to ensure statistical assumptions of normality were not violated. All statistical analyses were done using Statistical Analytical Systems (SAS) (SAS Institute, Cary, N.C., 1997). The General Linear Model (GLM) procedure was used to detect significant differences (P<0.05) in cumulative mortality between treatment groups (vaccinated and control) and between replicates (tanks) of these treatment groups, where replicate tanks were used. Significant differences were determined at P<0.05± standard error.

Results

Figure 1:
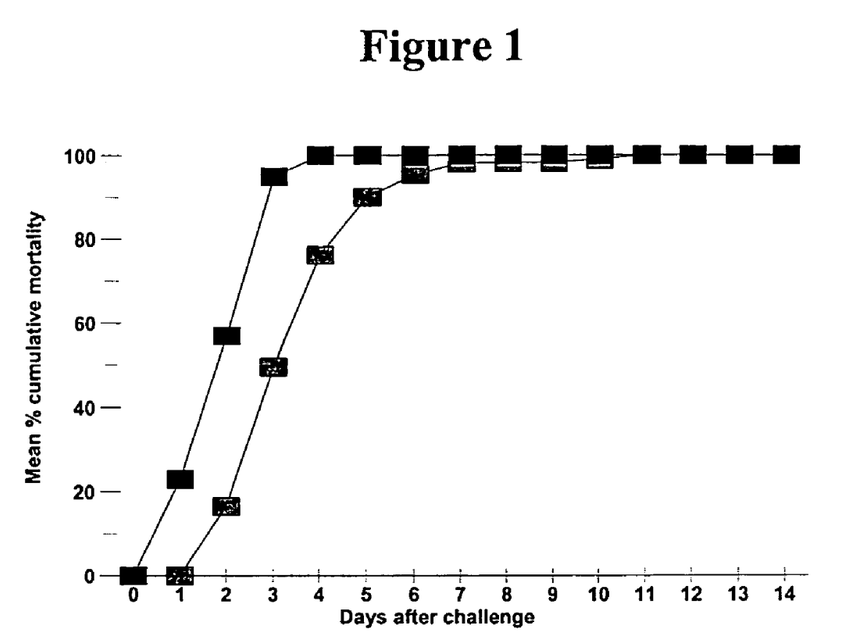
FIG. 1 shows the mean percent cumulative mortality of tilapia administered *S. iniae* vaccine by intraperitoneal (IP) injection and IP challenged with $2.6 \times 10^4$ CFU *S. agalactiae*/fish (□ vaccinates; ■ non-vaccinates).

The *S. iniae* vaccine preparation failed to protect tilapia against *S. agalactiae* infection. The mean percent mortality and RPS of *S. iniae* vaccinated and non-vaccinated tilapia following *S. agalactiae* challenge are shown in Table 1. Tilapia IP immunized with *S. iniae* and challenged with the *S. agalactiae* NRRL B-30607 isolate had an RPS of 0, where 100% of *S. iniae* vaccinated tilapia became infected with *S. agalactiae*. Significant differences in mortality between vaccinates and non-vaccinates were not noted. Mortality of vaccinates occurred sooner and was greater than mortality in the non-vaccinates (FIG. 1). Mortality began at 1 d and 2 d in the *S. iniae* vaccinated tilapia and non-vaccinates, respectively. One hundred percent cumulative mortality in the *S. iniae* vaccinates was reached at 4 d as compared to 11 d for non-vaccinates.

TABLE 1

Mean percent mortality and relative percent survival (RPS) of *S. iniae* intra-peritoneally (IP) vaccinated and non-vaccinated tilapia, *Oreochromis niloticus*, IP challenged with *S. agalactiae*[1].

| Treatment group | Water temp (° C.) | Average fish weight (g) | No. of Fish (Reps) | Route/Days Vaccinated | Challenge dose CFU/fish | Mean % mortality and (P value by GLM test) | RPS |
|---|---|---|---|---|---|---|---|
| Control or non-vaccinated | 26 | 30 | 100(5) | IP | 30 | $2.6 \times 10^4$ | 100 | |
| Vaccinated | 26 | 30 | 100(5) | IP | 30 | $2.6 \times 10^4$ | 100 (—) | 0 |

[1]Non vaccinates received tryptic soy broth (TSB) only.

EXAMPLE 2

The *S. agalactiae* vaccines of this invention were evaluated for efficacy against *S. agalactiae*. In contrast to the *S. iniae* vaccines of Example 1, the *S. agalactiae* vaccines were protective.

Materials and Methods

Tilapia

The tilapia were from stocks maintained at the ARS, USDA, Aquatic Animal Health Research Laboratory (Auburn, Ala.). Tilapia with mean weights of five and 30 g were acclimated in flow-through 57 l glass aquaria supplied with 0.5 l/h de-chlorinated water for 10 days prior to experiments. A light and dark period of 12 h: 12 h was maintained and aeration was supplied by an air stone. The fish were fed daily to satiation with AQUAMAX GROWER 400 (Brentwood, Mo.). Water quality was monitored, with dissolved oxygen, temperature and salinity measured daily using a YSI 85 oxygen conductivity, salinity, and temperature meter (Yellow Spring Instrument Co., Yellow Springs, Ohio). In all trials, daily water temperature averaged 31.68±0.08° C. or 26.3±0.03° C. and mean daily dissolved oxygen was 5.95±0.06 mg/l. To verify the *S. agalactiae*-free status of the fish, samples were obtained for bacterial culture by passing an inoculation loop into brain and kidney. Samples were streaked directly on sheep blood agar that were incubated at 27° C. for 24 to 48 h. *S. agalactiae* was not isolated from five randomly selected fish.

Vaccine Preparation

Vaccines were prepared by separate culture of *S. agalactiae* isolates (NRRL B-30608 and NRRL B-30607) in tryptic soy broth (TSB) and incubated in a shaker (70 RPM) water bath at 27° C. for 72–125 h. Cultures were treated with a final 3% neutral buffered formalin concentration for 24 h. The formalin treated culture was centrifuged at 7,000×g for 30 minutes and cell pellet and culture fluid separated. The cell-free culture fluid was concentrated five-fold on a 3 kDa Amicon column (S3Y3) using a Millipore Proflux M12 (Billerica, Mass.). The concentrated cell-free culture fluid was sterilized using a 0.22 Fm 1 l microbiological filter (Corning, Corning, N.Y.). Sixteen ml of the formalin-killed cells were added to 1 l of the sterilized concentrated cell-free culture fluid. The vaccine had an optical density of 1.9 at 540 nm. The number of colony forming units (CFU)/ml of *S. agalactiae* in the final vaccine preparation was estimated to be $4 \times 10^9$. The bacterial concentration was estimated by taking the optical density of the vaccine prior to killing by formalin. The actual number of CFU/ml was determined using a spiral autoplater and Qcount (Spiral Biotech, Norwood, Mass.). Non-vaccinates received concentrated tryptic soy broth (TSB) only. The vaccine cells were determined to be killed by lack of growth on sheep blood agar at 72 hours.

Vaccination Protocol

Intraperitoneal Administration

Three IP *S. agalactiae* vaccine trials (trials 2–4) were conducted. For trial 2, forty 5 g tilapia were divided into two groups of 20 fish each. For trial 3, two hundred 30 g tilapia were divided into 10 tanks of 20 fish each. Five replicate tanks of tilapia served as controls. For trial 4, one hundred and sixty 30 g tilapia were divided into six groups (3 replicate tanks of non-immunized controls and vaccinates) of 26–27 fish per group. Trials 2 and 4 were conducted at 32° C. and trial 3 was conducted at 26° C. For all trials, the vaccine was IP injected at a volume of 0.1 ml into tilapia. Control tilapia were IP injected with sterile TSB at the same volume.

Bath Immersion Administration

Two *S. agalactiae* vaccine immersion trials (trials 5–6) were performed at 32° C. For trial 5, one hundred and thirty 5 g tilapia were divided into two groups of 65 (control) and 65 (immunized) fish. Control tilapia were immersed in 1 l of 500 ml sterile water: 500 ml TSB for 20 min and, following immersion, 20–25 fish were placed in three replicate aquaria. Immunized fish were immersed in undiluted vaccine containing 16 ml bacterin and 1000 ml toxoid for 20 min with air and, following immersion, 2–25 fish were placed in three replicate aquaria. Five g tilapia did not tolerate the straight vaccine well, and 30 fish died following vaccination, which necessitated the need for dilution of vaccine. An additional 30 fish were immersed in diluted vaccine (500 ml vaccine: 500 ml sterile water) and distributed among replicate tanks to replace those lost during straight vaccine immersion. No additional mortality was noted following 30 days post vaccination. For trial 6, forty-five 30 g tilapia were divided into four groups of 11–12 fish each. Two groups of six fish each were immunized in 500 ml of undiluted vaccine (first dip), and another two groups of six fish each were immunized in the same vaccine solution (second dip) with air. First dip and second dip immunized fish were placed into separate aquaria. Control fish were immersed in TSB using the same procedure.

Experimental Challenge and Bacteriologic Sample Evaluation

At 30–64 days post-vaccination, the groups of vaccinates and non-vaccinates were weighed and IP challenged with 0.1 ml of a homologous (ARS-KU-MU-11B) or heterologous (ARS-KU-MU-3B) *S. agalactiae* isolate at cell concentrations ranging from $2.6 \times 10^3$ to $1.7 \times 10^6$ CFU/fish (Table 2) and monitored daily for clinical signs and mortality for 14 days. Infected tilapia were observed for behavioral and pathological signs of erratic swimming. Dead fish were removed twice a day and bacterial samples were obtained aseptically from the brain, anterior kidney, and intestine of 20% of morbid and dead fish to confirm the presence of *S. agalactiae*. Samples were cultured onto sheep blood agar (Remel, Lenexa, Kans.). Beta-hemolytic, oxidase-negative, and Gram-stained positive coccus colonies were identified as *S. agalactiae* using RAPID ID 32 STREP TEST (bioMérieux Vitek, Hazelwood, Mo.). The mean percent mortality and mean percent cumulative mortality of vaccinated and non-vaccinated tilapia for each trial was determined over a 14 d period. The efficacy of the vaccine was calculated as relative percent survival (RPS) (Amend, 1981).

Statistics

Significant differences in mortality between immunized and non-immunized controls after challenge for each trial were statistically analyzed by T-test and Lifetest according to procedures of the SAS Institute, Cary, N.C. (1997). Significant differences were determined at $P<0.05$. (See previous).

Results

Vaccine Efficacy

Figure 2:
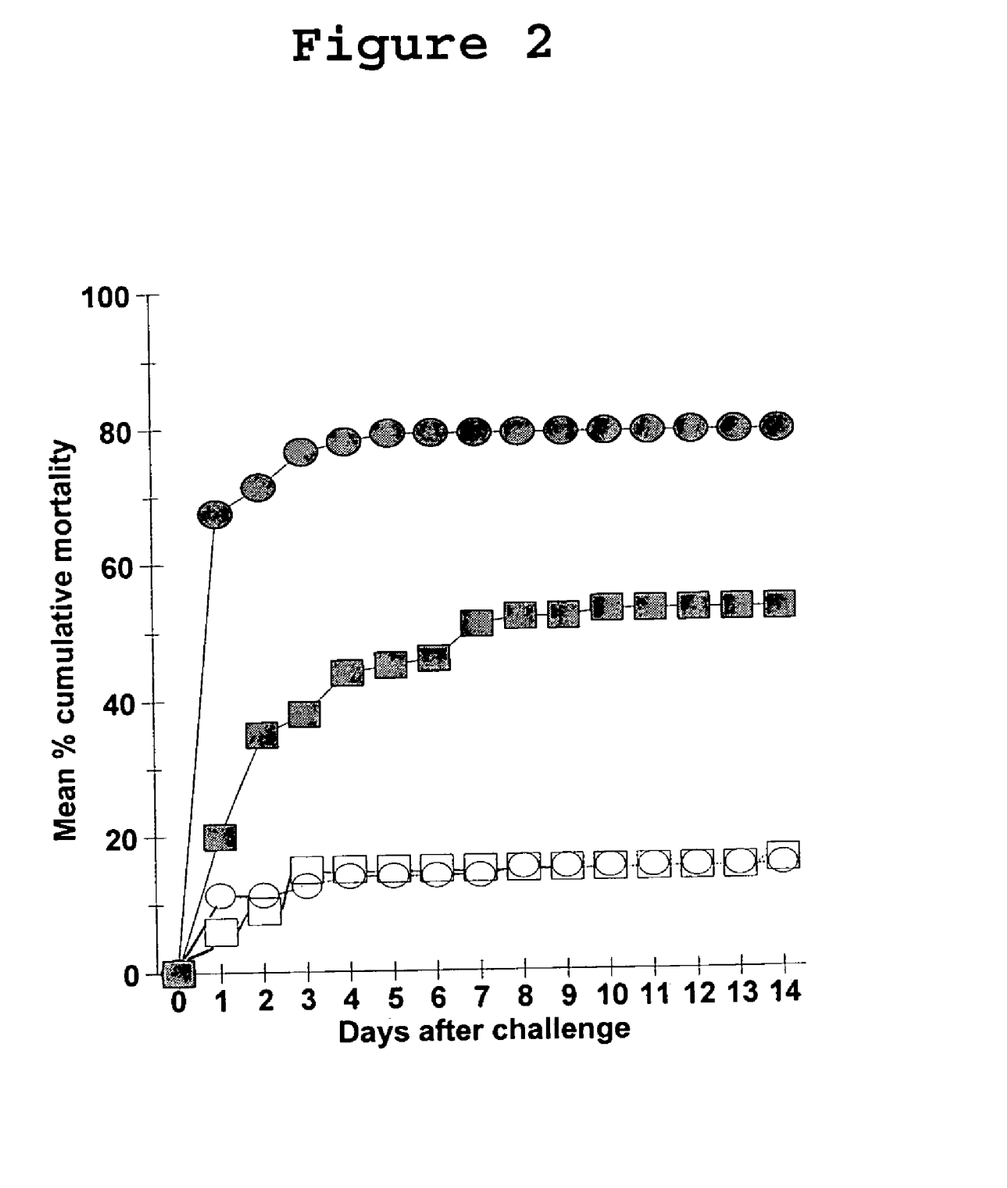
FIG. 2 shows the mean percent cumulative mortality of tilapia administered *S. agalactiae* vaccine (trials 3 and 4) by intraperitoneal (IP) injection and IP challenged with *S. agalactiae*. T; Trial 3 challenge dose $2.6 \times 10^3$ CFU/fish (■ vaccinates; □ non-vaccinates); Trial 4 challenge dose 1.5× $10^4$ CFU/fish (○ vaccinates; ● non vaccinates)

The mean percent mortality and RPS of *S. agalactiae* vaccinated and non-vaccinated tilapia following *S. agalactiae* challenge are shown in Table 2. In contrast to *S. iniae* IP vaccination and challenge with *S. agalactiae*, 30 g tilapia IP vaccinated with *S. agalactiae* vaccine and IP challenged following 64 and 30 d post-vaccination with $2.6 \times 10^3$ and $1.5 \times 10^4$ CFU/fish had excellent RPS values of 70 and 80 in trials 3 and 4, respectively. Water temperature (26 vs 32° C.) between trials 3 and 4 did not appear to influence the RPS results. FIG. 2 shows the daily mean percent cumulative mortality for *S. agalactiae* vaccinated and non-vaccinated fish after challenge with *S. agalactiae*. The mean percent cumulative mortality in the *S. agalactiae* vaccinates remained at 15–16% from day 3 to 14. Highly significant differences in mortality between immunized and non-immunized controls were seen in trials 3 and 4. No significant differences were noted between replicates of the treatments in trials 3 ($P=0.9117$) and 4 ($P=0.9510$). Smaller IP *S. agalactiae* vaccinated and non-vaccinated 5 g tilapia challenged with *S. agalactiae* had a RPS of 25 (trial 2, Table 2).

Figure 3:
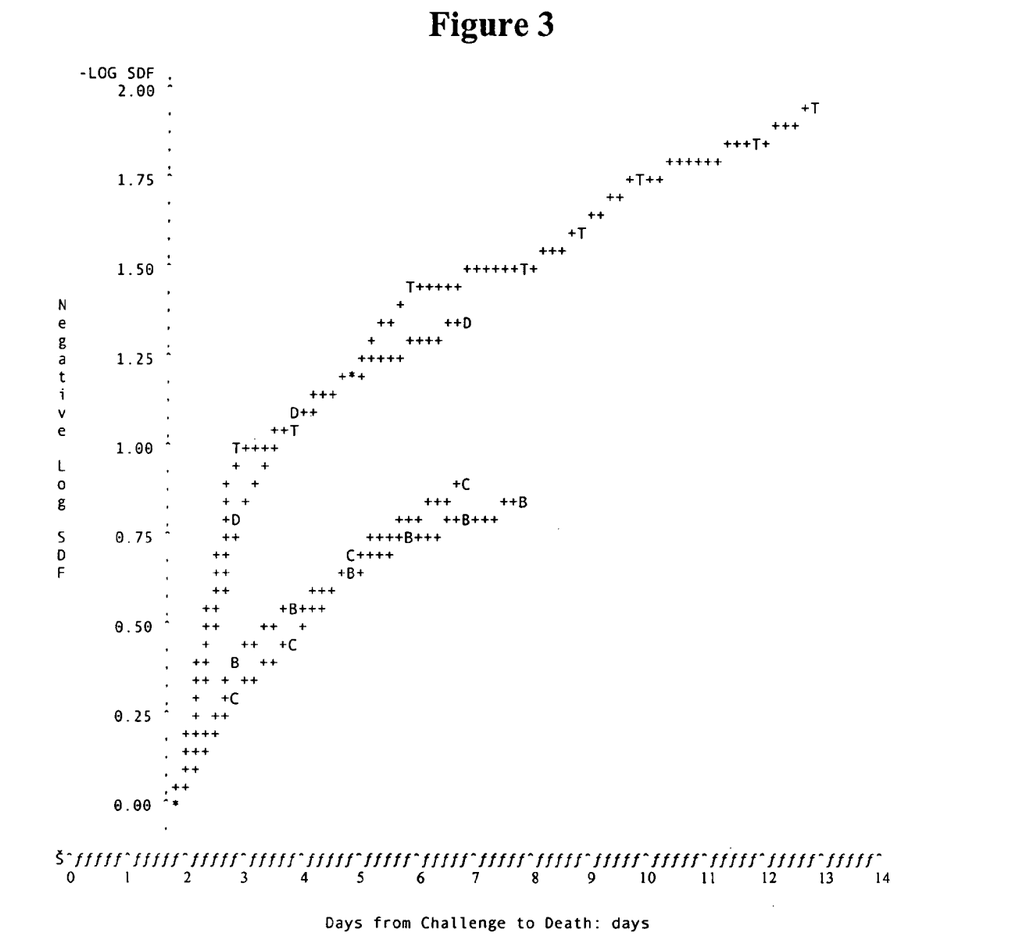
FIG. 3 shows the daily mortality of tilapia administered *S. agalactiae* vaccine (trials 5 and 6) by bath immersion and IP challenge with *S. agalactiae*. Trial 5 challenge dose $3.6 \times 10^5$ CFU/fish (T=non vaccinates; B=vaccinates); Trial 6 challenge dose $1.7 \times 10^6$ CFU/fish (C=vaccinates; D=non-vaccinates). Lifetest procedure (SAS Institute, Cary, N.C.)

Bath immersion vaccination of 5 g (trial 5) and 30 g (trial 6) tilapia followed by *S. agalactiae* challenge at $3.6 \times 10^5$ and $1.7 \times 10^6$ CFU/fish, respectively, produced a similar RPS of 34 (Table 2). Significant differences in mortality between immunized and non-immunized controls were seen in trial 5. No significant differences were noted between replicates of the treatments in trial 5 ($P=0.9798$) irrespective of vaccine (undiluted vs. diluted) treatment. In contrast, significant differences in mortality between immunized and non-immunized controls were not seen in trial 6. No significant differences ($P=0.7327$) in mortality were noted between replicates (first and second dips) of the treatments in trial 6. The 5 and 30 g vaccinates had a lower daily % cumulative mortality than the 5 and 30 g non-vaccinates. The 5 and 30 g non-vaccinates had very similar daily cumulative mortality, even though the 30 g fish were challenged with more than 10 times higher the dose than the 5 g fish. Mean percent mortality of non-vaccinates averaged 85 and mean percent mortality of vaccinates averaged 55 (Table 2). Mortality of non-vaccinated controls from both trials was greater than 50% at 1 d post challenge (FIG. 3). Fifty percent mortality of vaccinates was not reached until 5 d.

TABLE 2

Mean percent mortality and relative percent survival (RPS) of *S agalactiae* IP
vaccinated (trials 2–4) and bath immersion (BI) vaccinated (trials 5–6)
and non-vaccinated tilapia, *Oreochromis niloticus*, after IP challenge with
*S. agalactiae*.

| Trial No. | Treatment group | Water temp (° C.) | Average fish weight (g) | No. of Fish (Reps) | Route/Days Vaccinated | | Challenge dose CFU/fish | Mean % mortality and (P value by GLM test) | RPS |
|---|---|---|---|---|---|---|---|---|---|
| 2* | Control Non-vaccinated | 32 | 5 | 20(1) | IP | 46 | $1.1 \times 10^4$ | 67 | |
| | Vaccinated | 32 | 5 | 20(1) | IP | 46 | $1.1 \times 10^4$ | 50 (—) | 25 |
| 3+ | Control | 26 | 30 | 100(5) | IP | 64 | $2.6 \times 10^3$ | 53 | |
| | Vaccinated | 26 | 30 | 100(5) | IP | 64 | $2.6 \times 10^3$ | 16 (0.0020) | 70 |
| 4* | Control | 32 | 30 | 80(3) | IP | 30 | $1.5 \times 10^4$ | 76 | |
| | Vaccinated | 32 | 30 | 80(3) | IP | 30 | $1.5 \times 10^4$ | 15 (0.0024) | 80 |
| 5* | Control | 32 | 5 | 65(3) | BI | 30 | $3.6 \times 10^5$ | 84 | |
| | Vaccinated | 32 | 5 | 65(3) | BI | 30 | $3.6 \times 10^5$ | 55 (0.0303) | 34 |
| 6* | Control | 32 | 30 | 22(2) | BI | 34 | $1.7 \times 10^6$ | 86 | |
| | Vaccinated | 32 | 30 | 23(2) | BI | 34 | $1.7 \times 10^6$ | 56 (0.1982) | 35 |

*Heterologous challenge
+Homologous challenge

EXAMPLE 3

The *S. agalactiae* vaccines of this invention were again examined for efficacy in preventing infection by virulent *S. agalactiae*, and the effect on blood glucose levels was also determined.

The Materials and Methods, Vaccine Preparation, and Vaccination Protocol, were all as previously described in Example 2.

Sampling and Analysis of Blood

Prior to vaccination (0 h), ten fish were sampled for blood glucose. The fish were repetitively sampled for blood glucose at 2, 6, and 24 h post-vaccination. After 28 d post-vaccination, blood glucose was determined in ten vaccinates and ten controls prior to challenge (0 h pre-challenge). These fish were repetitively sampled for blood glucose at 2, 6, 24, 48, 72 h, and 312 h post challenge. The blood sample was taken using a tuberculin syringe and 27 gauge needle from the caudal vein. A 5 to 10 μL blood drop was placed onto a clean glass slide. The blood glucose concentration was determined by touching a ONE TOUCH ULTRA METER's (Lifescan, Miptas, Calif.) test strip top edge to blood drop at a 15 to 30° angle on a glass surface and allowing the blood to fill the confirmation window completely (Diouf et al., 2000). The glucose concentration was displayed in mg/dL in about 5 seconds. In a previous study, Evans et al. (2003b) determined the sensitivity of 20 mg/dL and an intra-assay variance of 3.25% (mean of 20.4±0.66 mg/dL) from ten replications of blood samples from healthy tilapia at acceptable DO levels. Furthermore, the glucose oxidase reaction measured by the glucose monitor was correlated with a calorimetric commercial laboratory method. The correlation coefficient (r) was 0.928 at a P<0.001.

Experimental Challenge

At 28 d post-vaccination, vaccinates and non-vaccinates were weighed and IP challenged with 0.1 mL of the *S. agalactiae* isolate at cell concentration of 1.5×105 CFU/mL and monitored daily for clinical signs and mortality for 13 d. Infected tilapia were observed for behavioral and pathological signs of erratic swimming. Dead fish were removed twice a day and bacterial samples were obtained aseptically from the brain, anterior kidney, and intestine and cultured onto SBA to confirm the presence of *S. agalactiae*. Beta-hemolytic, oxidase-negative, and Gram positive coccus colonies were identified as *S. agalactiae* using RAPID ID 32 STREP TEST (bioMérieux Vitek, Hazelwood, Mo.) (Evans et al., 2002). The cumulative treatment mortality was determined over a 13 d period. The efficacy of the vaccine was calculated as relative percent survival (RPS) (Amend, 1981).

Statistics

Data were statistically analyzed by ANOVA procedures followed by Duncan's Multiple Range test according to procedures of the SAS Institute (Cary, N.C., 1997). Significant differences in blood glucose levels between treatments at one time period and between all time periods for a single treatment were established at the p<0.001 for ANOVA and p<0.05 levels for Duncans. Correlation between blood glucose levels and mortality was performed by correlation procedures of SAS. Weights were analyzed as described above. Standard error was reported for all treatment mean blood glucose values.

Results

Figure 4:
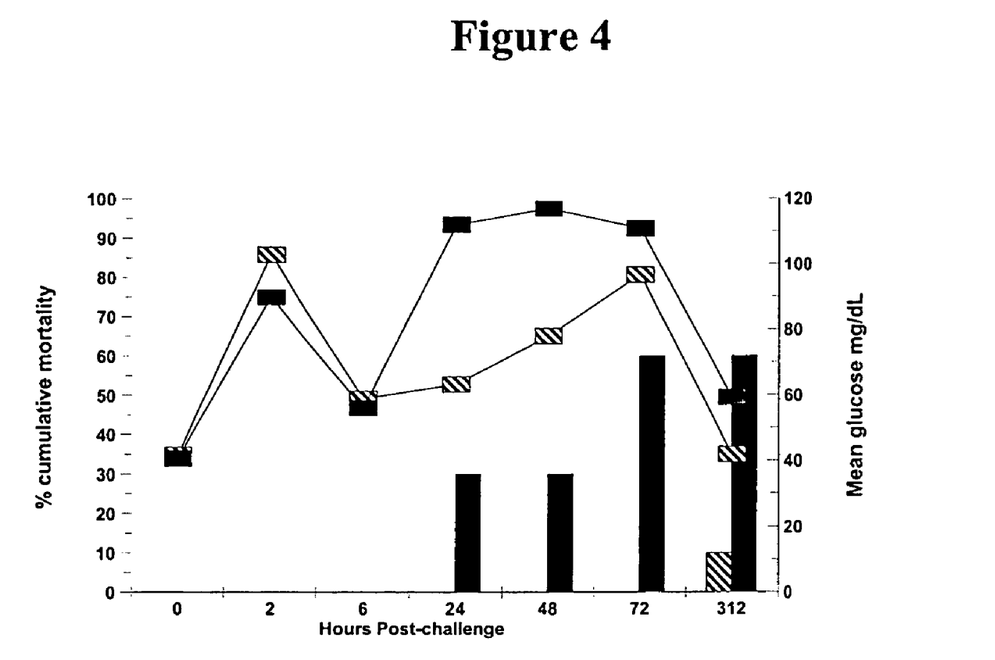
FIG. 4 shows the relationship between mean glucose values (mg/dL) (lines) and percent cumulative mortality (bars) in challenged tilapia at different time points post-challenge. Percent cumulative mortality in the 10 vaccinated (striped bar) and control (black bars) tilapia and mean blood glucose levels in the vaccinated (striped line) and control (black line) tilapia challenged with $1.5 \times 10^4$ CFU of *S. agalactiae* by IP injection.

Vaccinates had significantly higher blood glucose levels (97.9±9.90 mg/dL) than control fish (52.1±5.37 mg/dL) 2 h after injection of the vaccine (data not shown). Blood glucose levels of the vaccinates remained elevated at 6 h post-injection but not statistically elevated before returning to pre-injection levels at 24 h. No significant differences were noted in blood glucose between vaccinates and controls prior to vaccination (Oh) or at 6 and 24 h after vaccination. Blood glucose levels of controls IP injected with TSB were not significantly different at any time interval. No mortality was noted in controls or vaccinates 28 d post-vaccination. After challenge and infection with 1.5×10 4 CFU of *S. agalactiae* by IP injection, both vaccinates and controls had significantly higher blood glucose levels at 2, 24, 48, and 72 h than at pre-challenge 0 h (FIG. 4). Significantly elevated blood glucose levels between controls and vaccinates were noted at 24, 48, and 312 h. However, blood glucose levels of the vaccinates were lower than those of controls at these time periods. Glucose values for controls (117.0±14.09 mg/dL) peaked at 48 h. Blood glucose values of vaccinates (41.9±2.39 mg/dL) at 312 h were identical to those taken for vaccinates at 0 h prior to vaccination and challenge.

The controls displayed behavioral abnormalities 24 h after challenge which were typical of infected fish. Fish were aggregated at bottom of tank, showed no or slow response to food, and were lethargic. Mortality occurred considerably earlier in the controls than in vaccinates. Within 72 h after challenge, 60% mortality was noted in controls (FIG. 4). Only one vaccinate died at 96 h post challenge and none of the fish showed signs of infection or abnormal behavior. Relative percent survival was 83.4 at 312 h. FIG. 4 shows the relationship between mean glucose values and percent cumulative mortality of challenged vaccinates and controls over time. Blood glucose levels and mortality of the infected controls were significantly correlated ($r^2$=0.9236, P=0.0134). Moribund controls (N=4) were culture positive for S. agalactiae in brain, head kidney, and intestine.

It is understood that the foregoing detailed description is given merely by way of illustration and that modifications and variations may be made therein without departing from the spirit and scope of the invention.

We claim:

1. A composition comprising an immunologically effective amount of intact killed cells of isolated β-hemolytic Streptococcus agalactiae and a concentrated extract of a culture of β-hemolytic Streptococcus agalactiae.

2. The composition of claim 1 wherein said β-hemolytic Streptococcus agalactiae is encapsulated.

3. The composition of claim 2 wherein said β-hemolytic Streptococcus agalactiae comprises a strain having all the identifying characteristics of deposit accession number NRRL B-30607, a strain having all the identifying characteristics of deposit accession number NRRL B-30608, or mixtures thereof.

4. The composition of claim 1 wherein said concentrated extract consists essentially of extracellular products of said culture of β-hemolytic Streptococcus agalactiae.

5. The composition of claim 4 wherein said concentrated extract is free of cells, cell wall fragments, and intracellular components of said β-hemolytic Streptococcus agalactiae.

6. The composition of claim 1 wherein said concentrated extract comprises extracellular products of said culture of β-hemolytic Streptococcus agalactiae having a molecular weight greater than about 1 kDa.

7. The composition of claim 6 wherein said extracellular products have a molecular weights greater than about 2 kDa.

8. The composition of claim 7 wherein said extracellular products have a molecular weights greater than about 3 kDa.

9. The composition of claim 6 wherein said concentrated extract consists essentially of extracellular products of said culture of β-hemolytic Streptococcus agalactiae.

10. A method of protecting a fish against infection by Streptococcus agalactiae comprising administering the composition of claim 1 thereto.

11. The method of claim 10 wherein said fish is selected from the group consisting of golden shiners, bullminnows, bluefish, gulf menhaden, sea catfish, mullet, pinfish, Atlantic croaker, spot, weakfish, channel catfish, rainbow trout, eels, striped bass and their hybrids, sea bass, sea bream, turbot and tilapia.

12. The method of claim 11 wherein said fish is a tilapia.

13. The method of claim 10 wherein said composition is administered by intraperitoneal injection or bath immersion.

14. A method of protecting a fish against infection by Streptococcus agalactiae comprising administering the composition of claim 3 thereto.

15. A method of protecting a fish against infection by Streptococcus agalactiae comprising administering the composition of claim 4 thereto.

16. A method of protecting a fish against infection by Streptococcus agalactiae comprising administering the composition of claim 6 thereto.

17. A method of protecting a fish against infection by Streptococcus agalactiae comprising administering the composition of claim 9 thereto.

18. The composition of claim 1 wherein said β-hemolytic Streptococcus agalactiae was isolated from an infected fish.

* * * * *